(12) United States Patent
Flora et al.

(10) Patent No.: US 8,774,589 B2
(45) Date of Patent: Jul. 8, 2014

(54) INTERFEROMETER ADAPTER CAP FOR AN OPTICAL FIBER INSPECTION MICROSCOPE

(75) Inventors: Dennis Flora, Penacook, NH (US); Vincent Savage, Belmont, NH (US)

(73) Assignee: AFL Telecommunications LLC, Spartanburg, SC (US)

( * ) Notice: Subject to any disclaimer, the term of this patent is extended or adjusted under 35 U.S.C. 154(b) by 0 days.

(21) Appl. No.: 13/382,246

(22) PCT Filed: May 5, 2011

(86) PCT No.: PCT/US2011/035382
§ 371 (c)(1),
(2), (4) Date: Jan. 4, 2012

(87) PCT Pub. No.: WO2011/140357
PCT Pub. Date: Nov. 10, 2011

(65) Prior Publication Data
US 2013/0063720 A1    Mar. 14, 2013

Related U.S. Application Data

(60) Provisional application No. 61/331,439, filed on May 5, 2010.

(51) Int. Cl.
*G02B 6/00*    (2006.01)

(52) U.S. Cl.
USPC .......................................... 385/139; 356/498

(58) Field of Classification Search
USPC ............ 385/60, 134, 139; 356/450, 496, 498, 356/510
See application file for complete search history.

(56) References Cited

U.S. PATENT DOCUMENTS

| | | | |
|---|---|---|---|
| 4,248,821 A * | 2/1981 | Van Dellen | 264/135 |
| 5,917,595 A | 6/1999 | Norland et al. | |
| 6,381,397 B1 * | 4/2002 | Bevan et al. | 385/139 |
| 7,505,652 B2 | 3/2009 | Koudelka et al. | |
| 7,555,190 B2 | 6/2009 | Iwazaki et al. | |
| 7,561,775 B2 * | 7/2009 | Lin et al. | 385/139 |
| 2006/0187465 A1 | 8/2006 | De Groot | |
| 2008/0101757 A1 * | 5/2008 | Lin et al. | 385/139 |
| 2008/0310795 A1 * | 12/2008 | Parkman et al. | 385/60 |
| 2010/0027108 A1 | 2/2010 | Wilhelm et al. | |

\* cited by examiner

*Primary Examiner* — Charlie Peng
*Assistant Examiner* — Mary El Shammaa
(74) *Attorney, Agent, or Firm* — Sughrue Mion, PLLC

(57) ABSTRACT

An adapter cap including a cap body, a slot in the cap body, wherein the slot is configured to hold an optical flat, an attachment mechanism configured to attach the cap to an inspection device, and an alignment hole in the cap body, wherein the alignment hole is configured to hold an optical connector ferrule.

4 Claims, 6 Drawing Sheets

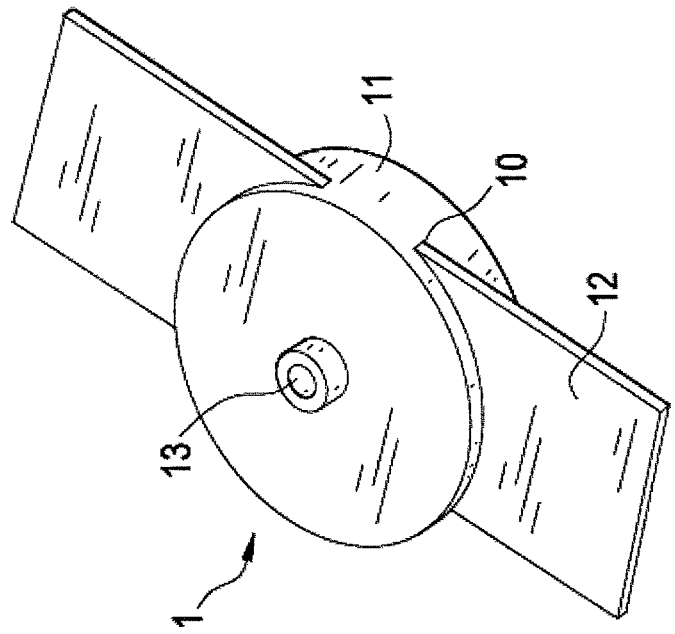

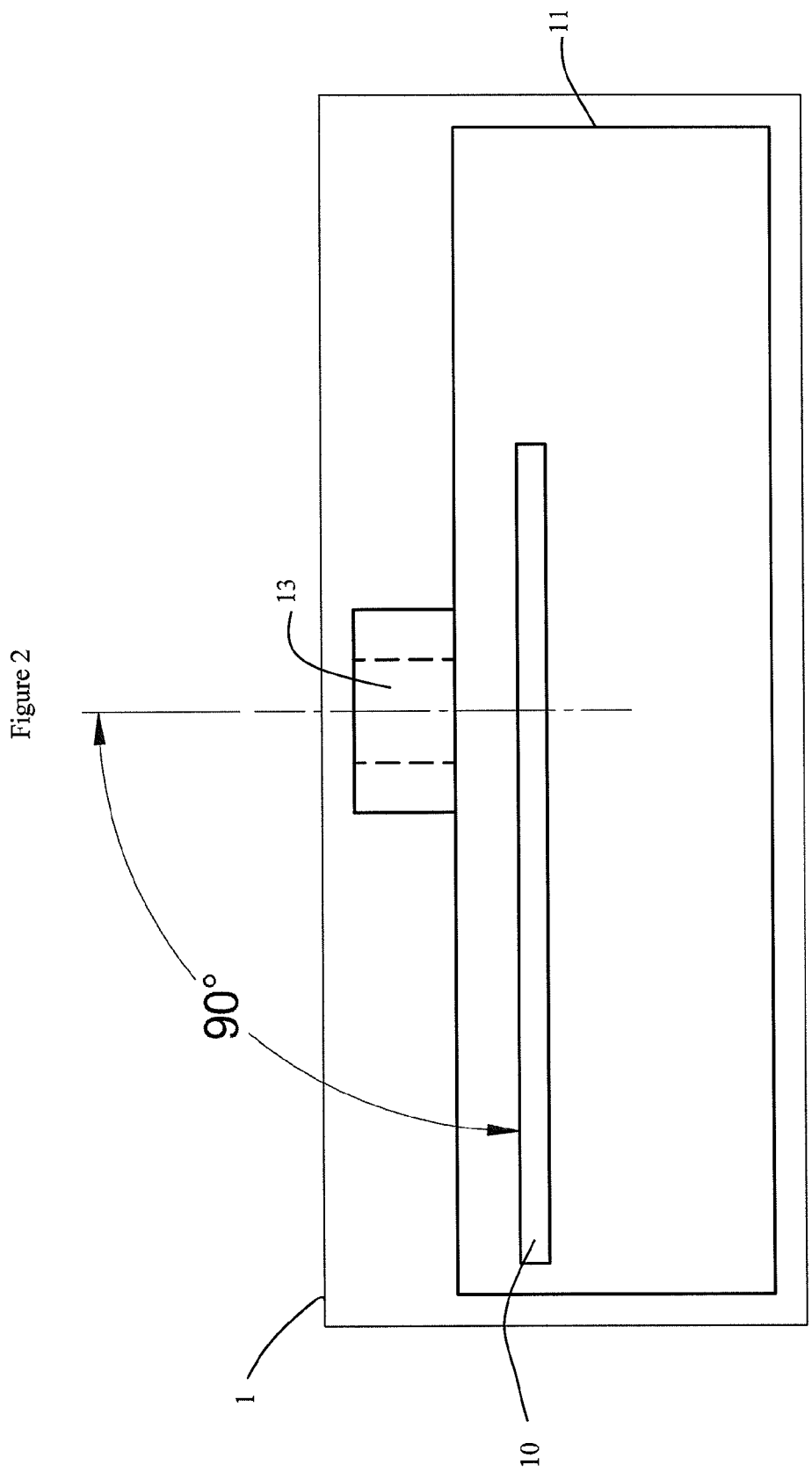

INTERFEROMETER ADAPTER CAP FOR AN OPTICAL FIBER INSPECTION MICROSCOPE

CROSS-REFERENCE TO RELATED APPLICATIONS

This application is based upon and claims the benefit of priority from U.S. Provisional Application No. 61/331,439, filed May 5, 2010 in the United States Patent and Trademark Office, the disclosure of which is incorporated herein in its entirety by reference.

BACKGROUND

1. Field

The invention is related to an interferometer adapter cap which can easily be incorporated attached to a fiber inspection device, such as a microscope. It could also be used to examine the "flatness" of the end of any small object with a suitable holder.

2. Related Art

A number of interferometer products tailored to the inspection of fiber optic connector ferrule end faces exist today. They are typically bench style units intended for production or laboratory use. Most are "non-contact" types which do not require physical contact with the connector under inspection. Some are "contact" types which are intended for the inspection of bare optical fiber cleave angles, which are crucial for successful fusion splicing.

The non-contact interferometers tend to be expensive due primarily to the high cost of the specialized optics and motion systems which they contain. Examples of these interferometers include the Micro Enterprises "Optispec" line and the Norland CC6000 "Connect-Chek" models.

Problems with the current interferometers include cost, ease of use and physical form factors. For example, interferometers typically exhibit high sensitivity to mechanical vibration, placing restrictions on the work area. They are also very expensive and require a high end PC for data processing at the time of this writing.

Therefore, there is a need for a lower cost apparatus that can be used to inspect connector ferrules. Portable microscopes are one such apparatus. They are typically in the shape of a hand held probe so that during normal use, they can be held in a variety of positions to probe large panels of connectors, such as in a networking room.

In order to use such a portable microscope, some mechanism for attaching the connector ferrules to the microscope is needed. Therefore, one objective of the invention is to provide an apparatus that allows for the low cost testing of connector end-face geometry, in the field or office, with low sensitivity to environmental factors (vibration, movement, etc.).

SUMMARY

Exemplary implementations of the present invention address at least the above problems and/or disadvantages and other disadvantages not described above. Also, the present invention is not required to overcome the disadvantages described above, and an exemplary implementation of the present invention may not overcome any of the problems listed above.

A first embodiment of the adapter cap includes a cap body; a slot in the cap body, wherein the slot is configured to hold an optical flat, an attachment mechanism configured to attach the cap to an inspection device, and an alignment hole in the cap body, wherein the alignment hole is configured to hold an optical connector ferrule.

Another feature of the adapter cap is that the alignment hole is further configured such that an axis of the hole is perpendicular to a plane of the optical flat.

BRIEF DESCRIPTION OF THE DRAWINGS

FIG. 1A is a top perspective view of an embodiment of the invention.

FIG. 2 is a side view of an embodiment of the invention.

DETAILED DESCRIPTION

Figure 1B:
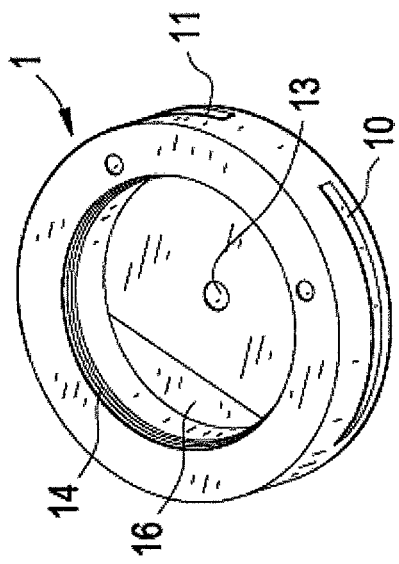
FIG. 1B is a bottom perspective view of an embodiment of the invention.

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. Descriptions of well-known functions and structures are omitted to enhance clarity and conciseness.

Hereinafter, the exemplary embodiments will be described with reference to accompanying drawings.

The invention is a low cost interferometer adapter "cap," which can easily be incorporated into many or all of the portable fiber inspection microscopes on the market today, or those yet to come, and those microscopes which uses a monochromatic light source. In a preferred embodiment, a blue monochromatic light is used. In many cases, only a method of holding the elements of the invention in proper mechanical orientation for the basic design of the microscope would be required. This is similar to the process, by which the adapter caps required for the varied optical fiber connectors in use today, are created for this type of inspection microscope.

FIG. 1A shows an embodiment of the inventive adapter cap 1. The cap 1 includes a narrow slot 10 in the side of the cap body 11 with an inner diameter and outer diameter. The inner diameter is sized so that the adapter can be attached to a microscope. In this exemplary embodiment, the inner diameter of the cap is secured to a microscope with a ⅞ inch×28 female thread and the outer diameter is approximately 1.25 inches. While the cap body 11 in this exemplary embodiment is cylindrical in shape, the cap body does not have to be cylindrical, as long as the adapter can be attached to a microscope. In addition, while the narrow slot 10 in this embodiment is offset from an axis of an alignment hole 13, the slot could be center with respect to the axis as well.

An optical flat 12, which could be a simple glass microscope slide, slides into the narrow slot 10 in the side of the cap body 11. Contact of the optical flat and the adapter cap is critical and is maintained by mechanical pressure similar to that provided by biological microscope stage clips. Only enough pressure to prevent movement during use is required. Because the optical flat can be removed from the adapter cap, it can be provided as a consumable item to help insure that it is always in good condition. The adapter cap also includes an alignment hole 13, into which a connector ferrule under inspection is inserted.

A bottom view of the adapter cap is shown in FIG. 1B. This embodiment contains screw threads 14 that can be used to attach the adapter cap to a fiber optic inspection microscope. The attachment mechanism can take many alternate forms such as a tapered fit, straight or tapered fit with clamping mechanism, straight or tapered fit with a latching mechanism (for example, an indented ball and spring). In addition, in this embodiment, an elevated portion 16 can act as a guide for an optical flat that is inserted into the slot 10.

FIG. 2 is a side view of the embodiment which shows the critical 90 degree angle of the axis of the alignment hole for the connector ferrule to the plane of the optical flat.

Figure 3:
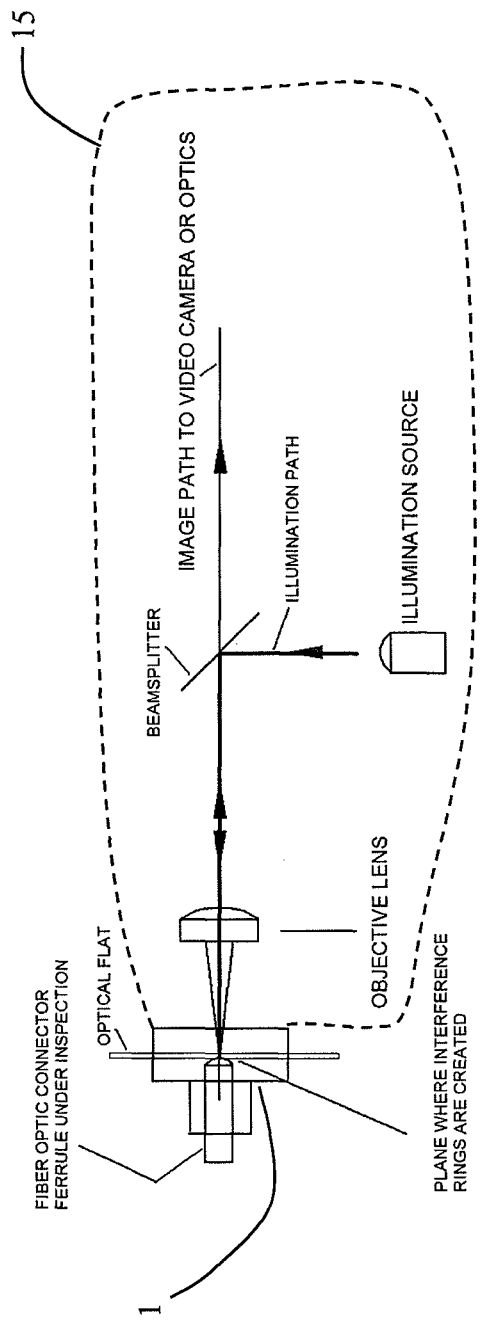
FIG. 3 a diagram showing how the invention is used with a microscope.

Next, the use of the adapter cap will be described. A fiber optic connector ferrule, previously inspected for cleanliness (possibly by the same inspection system), is inserted into the alignment hole 13 of a precise diameter and perpendicularity to a flat optical plate so that the connector ferrule can be held in the hole. This hole is coaxially aligned with the optical axis of the microscope by design. The fiber optic connector is then brought into physical contact with the optical flat. The adapter cap is then attached to the microscope 15. FIG. 3 is a schematic representation showing a connector in the adapter cap and the adapter cap 1 attached to the microscope 15, which may include an objective lens, beamsplitter and illumination source.

A series of Newton's rings are produced by this contact which are visible on the optical or video inspection end of the microscope (eye lens or video monitor). The rings have periodic light and dark values which are a result of the curvature manufactured into the end of the connector. The spacing of the rings is related to the radius of curvature of the connector and gross imperfections are readily observed as a disturbance in the circular shape of the rings. The phenomenon of Newton's rings was first described in 1664 by Robert Hooke and later analyzed by Sir Isaac Newton.

Figure 4:
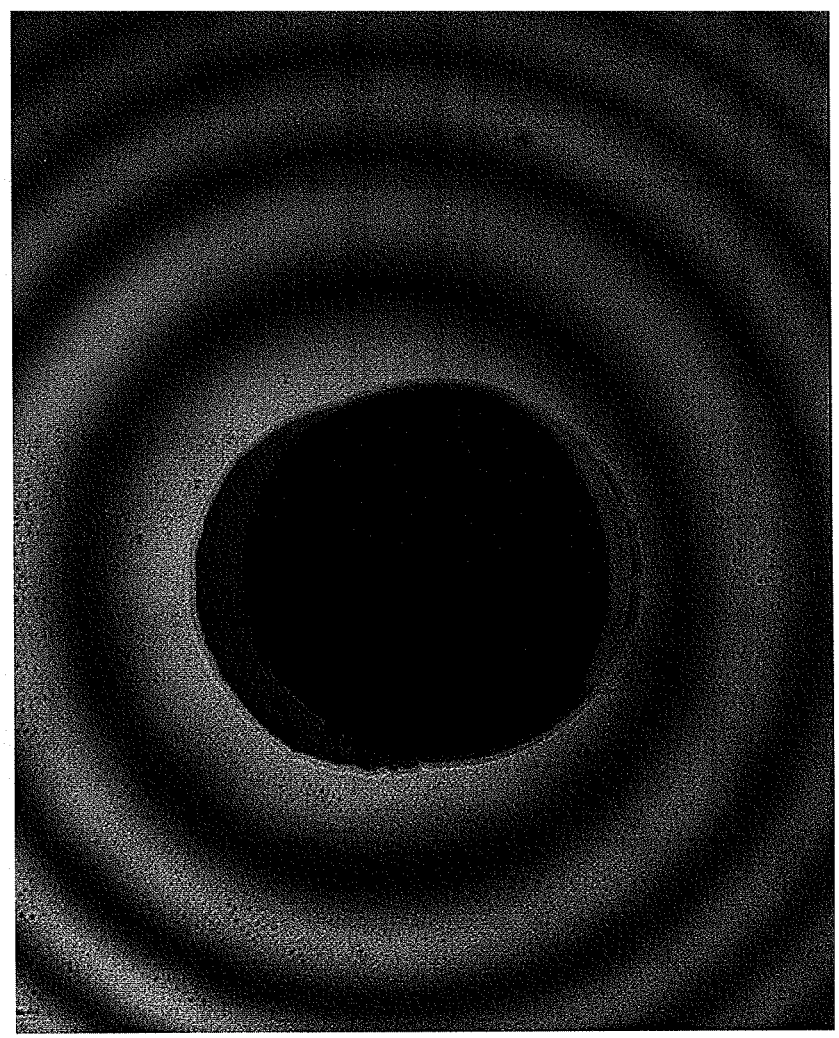
FIGS. 4 and 5 are illustrations of images that could be captured by an inspective microscope that uses an embodiment of the invention.
Figure 5:
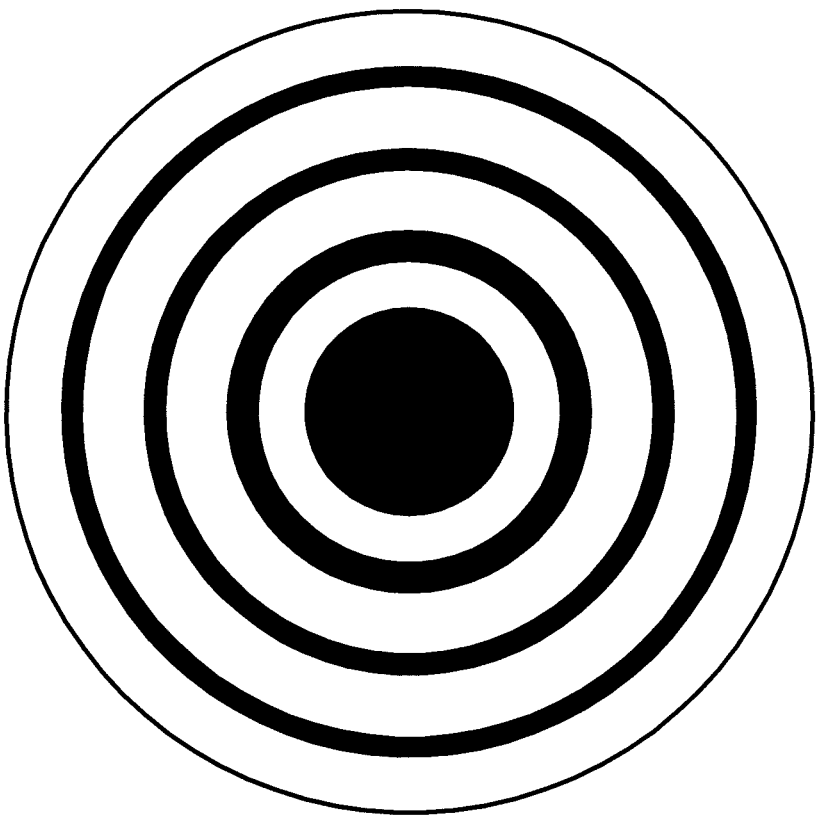

FIG. 4 is an illustration of an image that could be captured by an inspection system that uses the adaptive cap. The gray circle is the optical fiber end face, appearing against the white background of the connector ferrule. The concentricity of the rings indicates at a glance that the end radius of the connector is uniform in curvature. The darker black circle is caused by mechanical limitations of the lab-built prototype. On a properly finished connector, the dark circle would coincide with the gray circle that appears to protrude from beneath it, see for example FIG. 5.

Although a few exemplary embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An adapter cap comprising:
   a cap body;
   a slot in said cap body, wherein said slot is configured to hold an optical flat;
   an attachment mechanism configured to attach said cap to an inspection device; and
   an alignment hole in said cap body extending through said cap body, wherein said alignment hole is configured to hold an optical connector ferrule,
   wherein the slot comprises a pair of narrow slits in said cap body, at least one of the narrow slits extending from an interior surface of said cap body to an exterior surface of said cap body.

2. The cap of claim 1, wherein said alignment hole is further configured such that an axis of said hole is perpendicular to a plane of said optical flat.

3. The cap of claim 1, wherein said slot is configured to removably engage and hold, in the thickness direction, the optical flat.

4. The cap of claim 2, wherein said alignment hole is coaxial with the cap body.

* * * * *